United States Patent

Hansson et al.

[11] Patent Number: 6,134,754
[45] Date of Patent: Oct. 24, 2000

[54] LINE KEEP

[75] Inventors: Christer Hansson, Willow Street, Pa.; Fred P. Lampropoulos, Sandy, Utah; Arlin D. Nelson, Sandy, Utah; William Padilla, Sandy, Utah; Garlyn W. Hendry, Salt Lake City, Utah

[73] Assignee: Merit Medical Systems, Inc., South Jordan, Utah

[21] Appl. No.: 09/292,904

[22] Filed: Apr. 16, 1999

[51] Int. Cl.⁷ .............................. A44B 21/00; F16G 11/00
[52] U.S. Cl. .............................. 24/115 R; 24/18; 24/130; 24/543
[58] Field of Search .............................. 24/115 R, 134 P, 24/543, 18, 130, 129 R, 129 B, 300

[56] References Cited

U.S. PATENT DOCUMENTS

| | | | |
|---|---|---|---|
| 896,646 | 8/1908 | Litsch | 24/18 |
| 1,249,585 | 12/1917 | Zepp | 24/18 |
| 1,251,470 | 1/1918 | Bright | 24/130 |
| 1,251,778 | 1/1918 | Humble | 24/130 |
| 1,460,207 | 6/1923 | Mitchell | 24/18 |
| 1,612,396 | 12/1926 | Redmond | 24/115 R |
| 3,465,391 | 9/1969 | Armstrong | 24/115 R |
| 4,648,159 | 3/1987 | Dougherty | 24/18 |
| 5,056,197 | 10/1991 | Cohen | 24/543 |

Primary Examiner—Victor N. Sakran
Attorney, Agent, or Firm—Workman, Nydegger, Seeley

[57] ABSTRACT

A line keep includes a substantially flat base having a top surface and an opposing bottom surface. Positioned on the bottom surface is a pressure sensitive adhesive. Extending through the base between the top surface and opposing bottom surface are a pair of spaced apart apertures. A first prong upwardly projects from the top surface of the base and terminates in a horizontally disposed first finger disposed over the first aperture. A second prong projects from the top surface of the base adjacent to the second aperture and terminates at a second finger horizontally disposed over the second aperture. The first finger and second finger face in opposing directions and are configured to project through opposing sides of a vertical reference plane extending through the base between the first and second prong. The prongs can be selectively moved between an upstanding position and a folded position wherein the fingers are positioned adjacent to the line.

26 Claims, 4 Drawing Sheets

LINE KEEP

BACKGROUND OF THE INVENTION

1. The Field of the Invention

The present invention relates to line keeps and, more specifically, line keeps for securing catheters, guidewires, electrical lines, cables, and other elongated members.

2. Present State of the Art

There are becoming increasingly more minimally invasive surgical operations which require the insertion of lines within the body of a patient. The term "line" includes structures such as catheters, guidewires, miniaturized cameras, electrodes, electrical lines and the like, which are often feed into the body of a patient. Examples of operations which use such lines include orthoscopic surgeries and angioplasty procedures. Many conventional procedures require multiple lines of different type, size, and configuration to be either simultaneously or consecutively positioned within the body of the patient during a single operation. Many of these lines, particularly guidewires, are relatively small in diameter and can often range in length between 3 to 6 feet.

The use of lines and particularly multiple lines having different diameters, different lengths, and serving different functions can significantly add to the complexity of a surgery and can create inherent problems. Depending on the operation and the type of line used, the free end of the line projecting outside of the patient is simply rested on the patient or on the table either adjacent to the patient or between the patient's legs. Under such situations, it is often difficult to keep the free end of a line stationary when the line is not in use. Keeping the free end stationary is often critical so as to insure that the opposing distal end of the line within the patient remains at a desired location. It is also important to keep the free end of the line stationary so that the free end, which can often extend several feet, does not fall onto the floor or other potentially less sterile location and to insure that the line is kept out of the way of the surgeon.

Keeping each line at a fixed or defined location is also helpful in defining the type of line and in helping the surgeon locate the line. Some lines may have a similar exposed appearance but yet be shaped or positioned differently within the patient. Under such situations, it is desirable that the surgeon have some type of system that will enable the surgeon to easily and quickly distinguish between the lines. Smaller lines, particularly guidewires, can be difficult to locate among an array of other lines. This problem is exacerbated when during some surgical operations it is required that the room be darkened to better view a screen.

Another common problem with guidewires is that they can be difficult to pick up. That is, because of the small diameter of the guidewires, it can be difficult for a surgeon to pick up a the guidewire lying on a flat surface, such as an operating table.

Although elaborate and complex bracketing systems have been developed for assisting in the use of catheters and other types of lines, such systems are often very expensive, must be cleaned between uses, and have limited flexibility as to where and how they can be used.

There are also occasions not related to the medical field or industry when it is desirable to be able to quickly secure a line, such as electrical wiring, cables, rope, and tubing, at a desired location. It is also desirable if such lines can be removably secured for ease in manipulation and adjustment.

OBJECTS AND BRIEF SUMMARY OF THE INVENTION

Accordingly, it is an object of the present invention to provide line keeps which can be selectively used for securing a line, such as a catheter, guidewire, electrical line, cable, rope, or other elongated member, in a desired location, such as within a sterile or non-sterile environment.

Another object of the present invention to provide line keeps as above which are small and can be positioned at virtually any desired location.

Yet another object of the present invention is to provide line keeps as above which are configured to assist a surgeon or other user in picking up a small diameter line, such as a guidewire.

Still another object of the present invention is to provide line keeps as above which can be used to selectively restrict horizontal and linear sliding of the line, particularly a soft sided line such as a catheter or tubing.

Another object of the present invention is to provide line keeps which can be useful in distinguishing between different lines.

Finally, another object of the present invention is to provide line keeps as above which are inexpensive to manufacture and are disposable.

To achieve the foregoing and other objects of the present invention as embodied and broadly described herein, a line keep is provided. The line keep includes a thin base having a substantially flat top surface, an opposing substantially flat bottom surface, and a substantially elliptical perimeter. Positioned on the bottom surface is a pressure sensitive adhesive layer. This adhesive layer is covered by a removable protective layer.

Extending through the base between the top surface and the opposing bottom surface are a pair of spaced apart apertures. A first prong upwardly projects from the top surface of the base and terminates in a horizontally disposed first finger disposed over the first aperture. A second prong projects from the top surface of the base adjacent to the second aperture and terminates at a second finger horizontally disposed over the second aperture. The first finger and the second finger face in opposing directions in non-linear alignment and are configured to project through opposing sides of a vertical reference plane extending through the base between the first and second prong. The first and second prongs are configured such that when the prongs are viewed from a side, the prongs and base form the appearance of a closed channel in a vertical plane, the channel being configured to receive a desired line.

Also upwardly projecting from the top surface of the base so as to intersect with the reference plane are a plurality of ridges. Each ridge is in substantially parallel alignment with the pair of fingers. A center ridge is disposed between the first prong and second prong, a first side ridge is disposed along the perimeter of the base adjacent to the first prong, and a second side ridge is positioned adjacent to the perimeter of the base adjacent to the second prong. Each of the ridges extend between the prongs along the floor of the channel.

During use of the line keep, the protective layer is removed and the adhesive layer is pushed against a desired structure such that the line keep is securely position. As such, the line keep can be positioned on any surface at any desired orientation. Once the line keep is positioned, a line is snaked, bent, or otherwise manipulated in opposing directions so as to pass around each free end of the opposing fingers of the prongs. Alternatively, the prongs can be bent to one side to allow the line to pass therebetween. In either event, the line is received within the channel bounded by the prongs and base. In this position, the prongs prevent accidental removal of the line by either horizontal or vertical movement of the line. Removal of the line requires that the line again be bent or otherwise manipulated in opposing directions so as to pass around opposing fingers. Likewise, the fingers can again be bent to allow easy removal of the line.

In one embodiment of the present invention, the line keep is integrally molded as a discrete unit using an injection or other molding process from a plastic material. The integrally molded prongs and base are configured such that one or both of the prongs can be repeatedly and manually moved between an upstanding position and a folded position. In the folded position, each prong is folded or bent so that each corresponding finger is disposed adjacent to or is biased against the line positioned within the channel. In this embodiment, the prongs are configured so as to be substantially self-retained in the folded position. By moving the prongs into the folded position, the amount of free movement of a line within the channel is minimized, thereby further stabilizing the line. In addition, when the line comprises a soft flexible catheter, the prongs in the folded position can bias against the line so as to help prevent unwanted longitudinal or horizontal sliding of the line within the channel.

Based on the forgoing, the line keep provides an easy and quick mechanism for securing any desired line in a desired location. By substantially enclosing the line, the line keep prevents unwanted vertical and lateral displacement of the line. By bending the prongs into the folded position, the prongs can also bias against the line, thereby further limiting vertical and lateral displacement and also limiting longitudinal sliding of the line. This is particularly useful for soft sided lines such as catheters or tubing. The ridges projecting up from the base suspend the line off of the base. As a result, a surgeon or other user can easily grasp a small diameter line adjacent to the ridges for subsequent movement of the line. This is particularly useful for small diameter guidewires. As a result of the line keep being integrally molded as a single unit from plastic, the line keep can be inexpensively made and thus disposable. Finally, the line keeps can be made of different colors and different shapes SO as to help a user determine what type of line is associated with what line keep.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
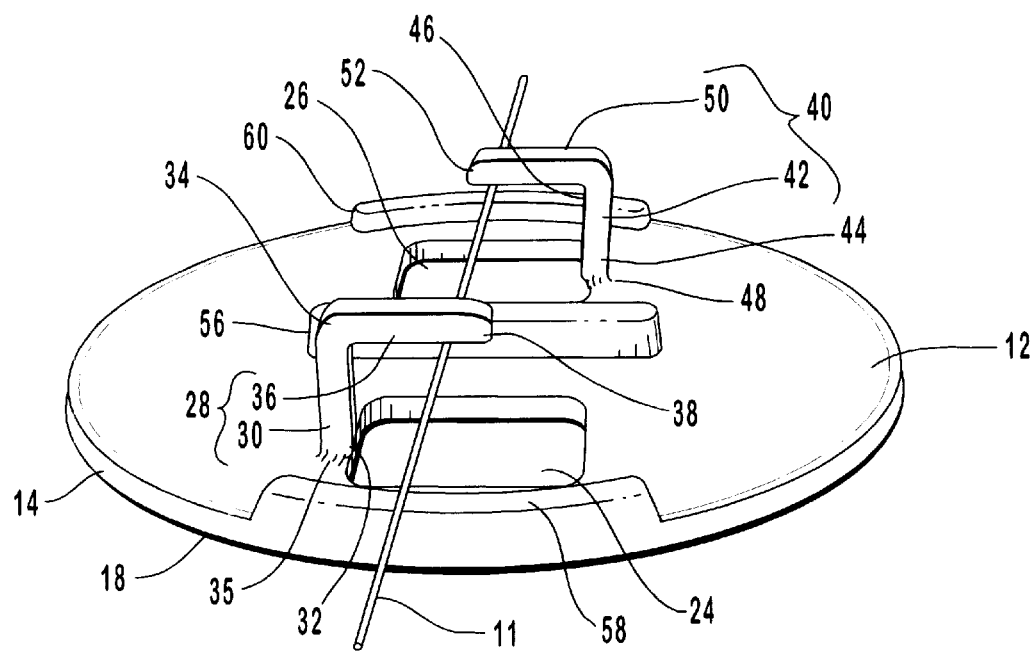
FIG. 1 is a perspective view of a line keep.

Depicted in FIG. 1 is one embodiment of an inventive line keep 10 incorporating features of the present invention. Line keep 10 is configured for selectively retaining a line 11 within a sterile field, such as in an operating room, and can be used in other non-sterile locations for non-medical related uses. As used in the specification and appended claims, the term "line" is broadly intended to include elongated, small diameter members such as catheters, tubing, guidewires, positioning wires, cords, electrical lines, rope, cable, and the like. Line keep 10 can be used with both medical and non-medical related products.

Figure 2:
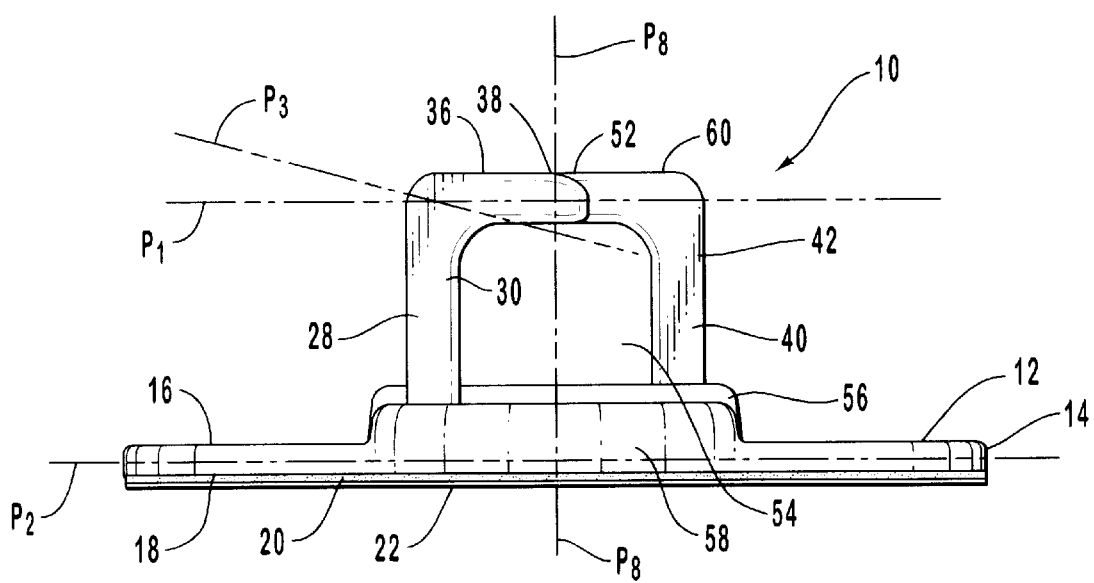
FIG. 2 is a side view of the line keep shown in FIG. 1.

As depicted in FIGS. 1 and 2, line keep 10 includes a thin plate like base 12 having a substantially flat top surface 16 and an opposingly substantially flat bottom surface 18. Each surface 16 and 18 extends to a perimeter edge 14. In the embodiment depicted, perimeter edge 14 has a substantially elliptical configuration. In alternative embodiments, perimeter edge 14 can have any desired polygonal configuration, such as circular or square, or can have an irregular configuration.

In one embodiment of the present invention, means are provided for securing base 12 to a discrete structure. By way of example and not by limitation, positioned on bottom surface 18 is a pressure sensitive adhesive layer 20. Disposed over adhesive layer 20 is a removable protective layer 22. Accordingly, when it is desired to secure base 12 to a desired structure, protective layer 22 is manually removed and adhesive layer 22 is pushed against the desired structure. As a result, line keep 10 can be securely mounted to virtually any desired structure within an operating room such as a patient's gown, the operating table, a wall, or surrounding operating equipment. Line keep 10 can also be mounted directly onto the body of a patient. When the operation or intended use of line keep 10 is complete, line keep 10 can be removed by simply pulling it from the structure. The present invention envisions that there are a variety of different types of adhesives that can be used. Furthermore, in alternative embodiments, conventional latching and clipping members can also be used for securing base 12 to a desired structure.

As depicted in FIG. 1, extending through base 12 between top surface 16 and bottom surface 18 is a first aperture 24 and a spaced apart second aperture 26. In an alternative embodiment, it is also envisioned that first and second apertures 24 and 26 can be integrally formed as a single enlarged aperture. Mounted on top surface 16 of base 12 is a first prong 28. First prong 28 includes a first post 30 vertically projecting on top surface 16. First post 30 has a mounting end 32 and an opposing top end 34. Mounting end 32 of first post 30 is secured at a first location 35 adjacent to first aperture 24. First prong 28 also includes a first finger 36. First finger 36 orthogonally projects from top end 34 of first post 30 and terminates at a free end 38. Free end 38 is vertically disposed over first aperture 24.

Also mounted on base 12, spaced apart from first prong 28, is a second prong 40. Second prong 40 includes a second post 42 vertically projecting from top surface 16 of base 12. Second post 42 has a mounting end 44 and an opposing top end 46. Mounting end 44 is positioned at a second location 48 positioned adjacent to second aperture 26. Second prong 40 also includes a second finger 50. Second finger 50 orthogonally projects from top end 46 of second post 42 to a free end 52. Free end 52 is vertically disposed over second aperture 26. First finger 36 and second finger 50 face in opposing directions and are spaced apart so as to not be in linear alignment.

Apertures 24 and 26 facilitate in the manufacturing process of forming prongs 28 and 40 on base 12. In alternative embodiment, however, apertures 24 and 26 are not required.

In the embodiment depicted in FIG. 2, first finger 36 and second finger 50 are each substantially horizontally disposed in a horizontally disposed first plane $P_1$. Plane $P_1$ is substantially parallel with a horizontal plane $P_2$ in which base 12 is disposed. In alternative embodiments, it is also envisioned that finger 36 and/or finger 50 can be inclined relative to plane P1. For example, first finger 36 can be inclined so as to be disposed in a plane $P_3$ which is angled relative to plane $P_1$. Similarly, although posts 30 and 42 are depicted as being vertically oriented, the present invention also envisions that post 30 and/or post 42 can be disposed at an angle, relative to a vertical axis, in any direction.

Figure 3:
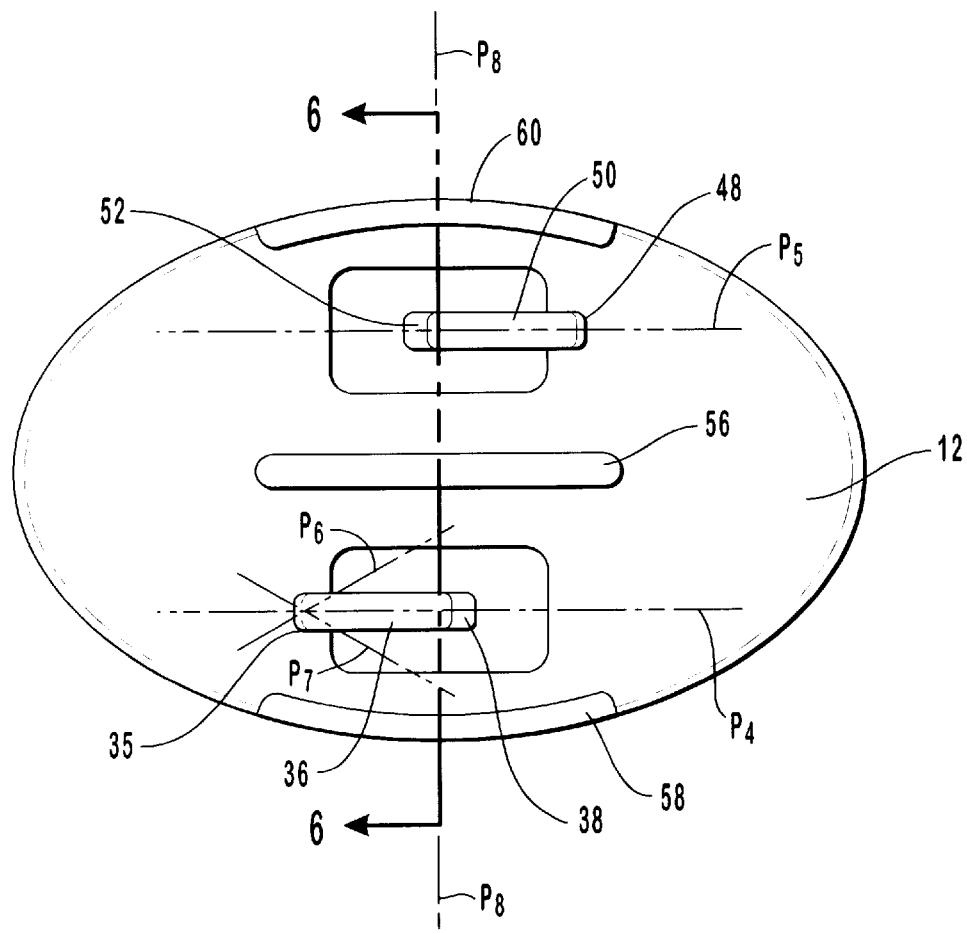
FIG. 3 is a top view of the line keep shown in FIG. 1.

As depicted in FIG. 3, first finger 36 is disposed in a vertical plane $P_4$ while second finger 50 is disposed in a vertical plane $P_5$. In the embodiment depicted, planes $P_4$ and $P_5$ are spaced apart and are in substantially parallel alignment. In alternative embodiments, finger 36 and/or finger 50 can be angled relative to planes $P_4$ and $P_5$. For example, first finger 36 can be disposed in planes $P_6$ or $P_7$ which are angled relative to plane $P_4$.

Figure 4:
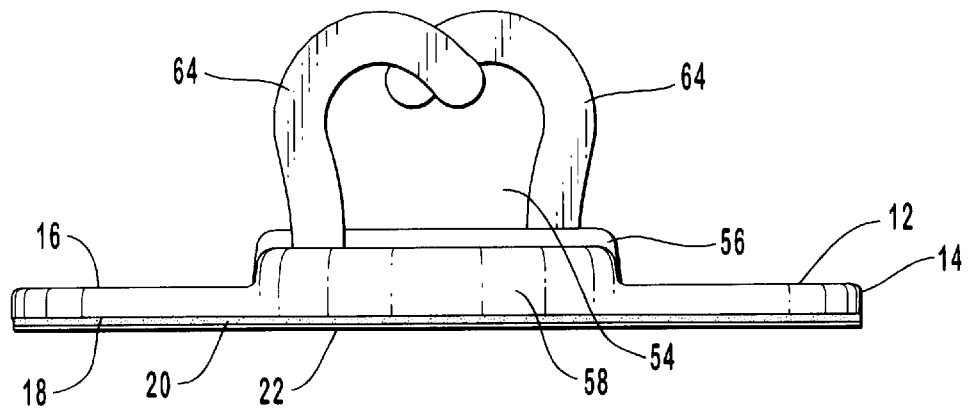
FIG. 4 is a side view of an alternative design of the prongs shown in FIG. 1.
Figure 5:
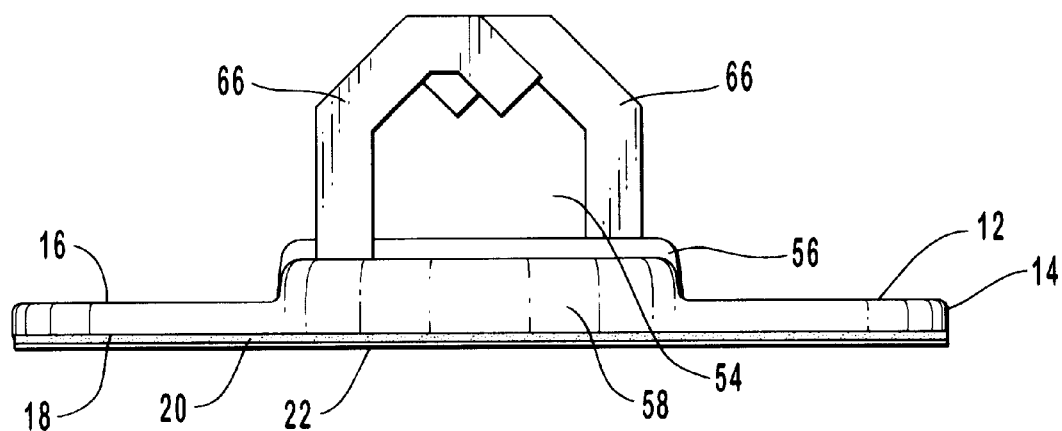
FIG. 5 is a side view of an alternative design of the prongs shown in FIG. 1.

The present invention also envisions that prongs 28 and 40 can come in a variety of different configurations. For example, depicted in FIG. 4 is a prong 64 have a hook like configuration while FIG. 5 depicts a prong 66 having a finger that projects in angled sections.

Returning to FIGS. 2 and 3, free end 38 of first finger 36 and free end 52 of second finger 50 are configured to project into opposing sides of a reference plane $P_8$. That is, reference plane $P_8$ can be positioned so as to extend through each finger 36 and 50. Reference plane $P_8$ is also vertically oriented so as to extend through base 12 between first location 35 and second location 48. In the embodiment depicted, fingers 36 and 50 are configured to orthogonally intersect with reference plane $P_8$ both in horizontal plane $P_1$ and in corresponding vertical planes $P_4$ and $P_5$. The present invention also envisions that when one of fingers 36 or 50 orthogonally intersects with vertically oriented reference plane $P_8$ in a horizontal plane, the other finger 36 or 50 also intersects with reference plane $P_8$ from the opposing side thereof but not necessarily orthogonally. Prongs 28 and 40 are also configured such that when viewed from the side, as shown in FIG. 2, the combination of base 12, first prong 28, and second prong 40 form the appearance of a channel 54 through which line 11 can be disposed. In the embodiment depicted, channel 54 has a closed perimeter. In alternative embodiments, channel 54 can have angled openings.

The present invention also includes means for supporting line 11 off of base 12 when line 11 is disposed between first prong 28 and second prong 40. By way of example and not by limitation, depicted in FIGS. 1, 3 and 6, a plurality of spaced apart ridges upwardly project from base 12 and are disposed so as to intersect with reference plane $P_8$ The plurality of ridges include an elongated center rigid 56 upwardly projecting from base 12 between prongs 28 and 40; a first side rigid 58 upwardly projecting from base 12 adjacent to first prong 28; and a second side rigid 60 upwardly projecting from base 12 adjacent to second prong 40. Each of ridges 56, 58, and 60 is disposed in substantially parallel alignment with fingers 38 and 50 and, as depicted in the side elevation view of FIG. 2, longitudinally extend between and beyond posts 28 and 40. As such, each rigid 56, 58, and 60 extends across the floor of closed channel 54.

Figure 6:
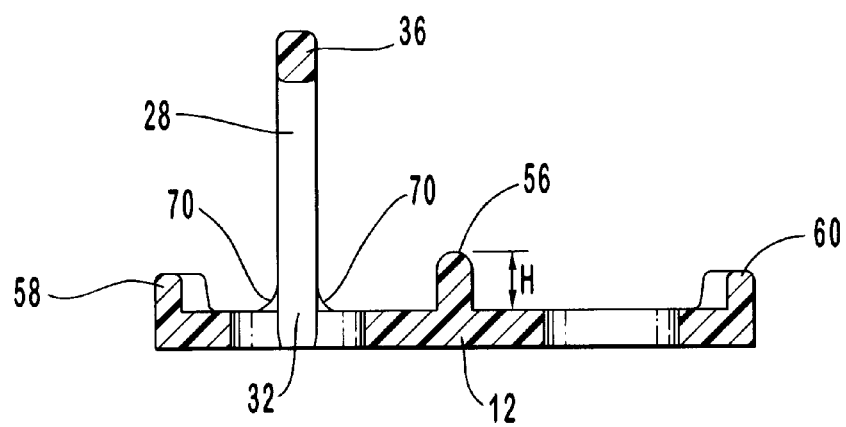
FIG. 6 is a cross sectional side view of the line keep shown in FIG. 3 taken along section line 6—6.

In alternative embodiments, only one or combinations of the ridges can be used. Positioning of the side ridges 58 and 60 facilitates a user in picking up a line either adjacent to line keep 10 or on top of line keep 10. As depicted in FIG. 6, ridges 56, 58, and 60 typically have a height H extending above base 12 in a range between about 0.15 cm to about 0.7 cm with about 0.25 cm to about 0.5 cm being more preferred. The plurality of ridges also function to prevent line 11 from getting stuck to adhesive layer 22 which may be exposed through apertures 24 and 26.

To facilitate use of line keep 10, protective layer 22 is removed and adhesive layer 20 is pushed against a desired structure such that line keep 10 is securely position. Using this process, line keep 10 can be positioned on any surface at any desired orientation. One or more line keeps 10 are preferably positioned such that channel 54 of each line keep 10 is aligned with the desired placement for the corresponding line 11. Once line keep 10 is positioned, line 11 is snaked, bent, or otherwise manipulated in opposing directions so as to pass around each free end of fingers 36 and 50 such that line 11 is received within channel 54. In this position, prongs 28 and 40 prevent accidental removal of line 11 by either horizontal or vertical movement of line 11. Removal of line 11 requires that line 11 again be bent or otherwise manipulated in opposing directions so as to pass around opposing fingers 36 and 50.

In one embodiment of the present invention, line keep 10, including base 12, ridges 56, 58, and 60, and prongs 28 and 40, is integrally molded as a discrete unit using an injection or other molding process from a plastic material. Examples of available plastics include polycyclohexylene dimethylene terephthalate (PCTG) and polyethylene terephthalate glycol comonomer (PETG). PCTG can be purchased from the Eastman Chemical Company under the tradename EASTAR in grades such as DN003, DN004, and DN007. Of course, line keep 10 can also be made of other materials such as other plastics or composites.

Figure 7:
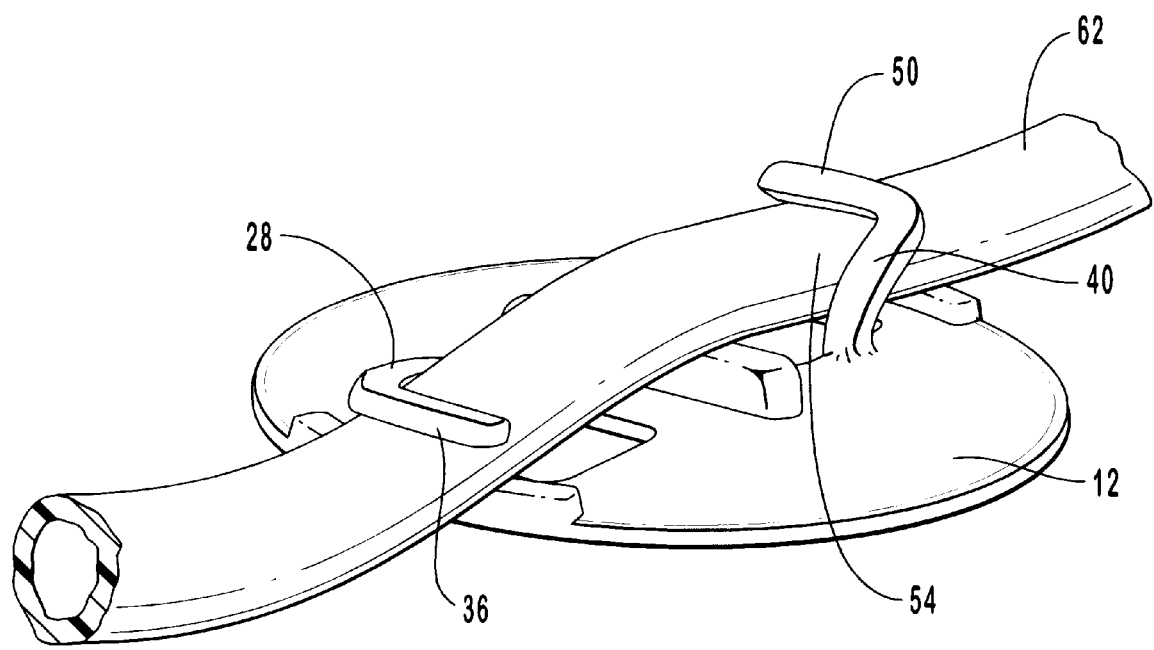
FIG. 7 is a perspective view of the line keep shown in FIG. 1 having the prongs thereof moved into a folded position against a catheter.

In one embodiment, the integrally molded prongs 28 and 40 and base 12 are configured such that one or both of prongs 28 and 40 can be repeatedly and manually moved between an upstanding position as shown in FIGS. 1–3 and a folded position as depicted in FIG. 7. In the folded position, each prong 28 and 40 is folded or bent so that each corresponding finger 36 and 50 is disposed adjacent to or is biased against a line 62 positioned within channel 54. In this embodiment, prongs 28 and 40 are configured so as to be substantially self-retained in the folded position. That is, prongs 28 and 40 do not resiliently spring back into the upstanding position but rather must be manually folded back into the upstanding position. By moving prongs 28 and 40 into the folded position, the amount of free movement of a line within channel 54 is minimized, thereby further stabilizing the line. In addition, when the line comprises a soft flexible material, such as catheter line 62 depicted in FIG. 5, prongs 28 and 40 in the folded position can bias against the line so as to help prevent unwanted longitudinal or horizontal sliding of the line within channel 54.

Depicted in FIG. 6, to help prevent fatigue failure of prongs 28 and 40 as they are moved between the upstanding and folded position, fillets 70 can be formed where mounting end 32 secures to base 12. In embodiments where prongs 28 and 40 can be selectively moved between the folded and upstanding position, line keep 10 can be integrally molded from PCTG or PETG as set forth above. Materials which enable prongs 28 and 40 to be selectively moved between the folded and upstanding position typically have a Flexural Strength at Yield in a range between about 8,000 psi and about 12,000 psi with about 9,000 psi to about 11,000 psi being more preferred. In yet other embodiments, line keep 10 can also be made from resilient materials wherein prongs 28 and 40 resiliently return back to their normal upstanding position whenever bent or folded.

The present invention also envisions that a plurality of line keeps 10 can be made in different colors or base 12 can be made in different shapes so as to help a user to identify what line is secured thereto. For example, a blue colored line keep 10 can be used for securing a catheter line communicating with a vein while a red colored line keep 10 can be used for securing a catheter line communicating with an artery. Line keep 10 can also be made of florescent or glow-in-the-dark materials so as to help a user locate the line keeps.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A line keep comprising:
    (a) a base having a top surface and an opposing bottom surface, the base bounding a first aperture extending through the base between the top surface and the bottom surface;
    (b) a first prong upwardly projecting from the top surface of the base at a first location adjacent to the first aperture and terminating at a freely exposed first finger, at least a portion of the first finger being in alignment with the first aperture;
    (c) a second prong upwardly projecting from the top surface of the base at a second location spaced apart from the first prong, the second prong terminating at a freely exposed second finger; and
    (d) a plurality of spaced apart discrete ridges which upwardly project from the top surface of the base, each of the plurality of discrete ridges intersecting the reference plane.

2. A line keep as recited in claim 1, wherein the base further bounds a second aperture extending through the base between the top surface and the bottom surface, the second aperture being spaced apart from the first aperture and disposed adjacent to the second prong.

3. A line keep as recited in claim 1, wherein the second finger is disposed in vertical alignment with the second aperture.

4. A line keep as recited in claim 1, wherein the first prong and the second prong are configured such that the first finger and the second finger project into opposing sides of a vertically oriented reference plane disposed between the first location and the second location when the base is horizontally disposed.

5. A line keep as recited in claim 4, wherein the second finger orthogonally intersects the reference plan in a horizontal plane.

6. A line keep as recited in claim 1, wherein the first finger and the second finger are each substantially disposed in a horizontal plane that is parallel with the base.

7. A line keep comprising:
    (a) a base having a top surface and an opposing bottom surface;
    (b) a first prong upwardly projecting from the top surface of the base at a first location and terminating at a freely exposed first finger, the first finger at least partially horizontally projecting over the base and being disposed in a vertical first plane longitudinally extending through the first finger when the base is horizontally disposed; and
    (c) a second prong upwardly projecting from the top surface of the base at a second location spaced apart from the first prong, the second prong terminating at a freely exposed second finger, the second finger at least partially horizontally projecting over the base and being disposed in a vertical second plane longitudinally extending through the second finger, the vertical first plane and the vertical second plane being spaced apart, the first finger and second finger projecting into opposing sides of a vertically oriented reference plane disposed between the first location and the second location when the base is horizontally disposed, the first finger orthogonally intersecting the vertically oriented reference plane in a horizontal plane.

8. A line keep as recited in claim 7, wherein the first prong comprises a first post orthogonally projecting from the base to a top end, the first finger projecting from the top end of the first post.

9. A line keep as recited in claim 7, wherein the first finger and the second finger are each disposed in a single horizontal plane that is substantially parallel with the base.

10. A line keep as recited in claim 7, wherein the vertical first plane and the vertical second plane are disposed in substantially parallel alignment.

11. A line keep as recited in claim 7, further comprising means for securing the base to a discrete structure.

12. A line keep as recited in claim 7, further comprising means for supporting a line off of the base when the line is disposed between the first location and the second location.

13. A line keep as recited in claim 7, wherein the first pong is configured such that the first prong can be selectively folded over and be self-retained in that position.

14. A line keep comprising:
    (a) a base having a top surface, an opposing bottom surface, and an outside perimeter;
    (b) a first prong upwardly projecting from the top surface of the base at a first location and terminating at a freely exposed first finger;
    (c) a second prong upwardly projecting from the top surface of the base at a second location spaced apart from the first prong, the second prong terminating at a freely exposed second finger, the first finger and second finger being configured so as to project into opposing sides of a vertically oriented reference plane disposed between the first location and the second location when the base is horizontally disposed; and
    (d) a plurality of spaced apart discrete ridges which upwardly project from the top surface of the base, each of the plurality of discrete ridges intersecting the reference plane.

15. A line keep as recited in claim 14, where the first finger and the second finger project in substantially opposing directions.

16. A line keep as recited in claim 14, further comprising an adhesive layer disposed on the bottom surface of the base.

17. A line keep as recited in claim 14, wherein the first prong and the second prong are aligned to bound a closed channel when the first pong is orthogonally viewed from the side thereof.

18. A line keep comprising:
   (a) a base having a top surface, an opposing bottom surface, and an outside perimeter;
   (b) a first prong upwardly projecting from the top surface of the base at a first location and terminating at a freely exposed first finger;
   (c) a second prong upwardly projecting from the top surface of the base at a second location spaced apart from the first prong, the second prong terminating at a freely exposed second finger, the first finger and second finger projecting into opposing sides of a vertically oriented reference plane disposed between the first location and the second location when the base is horizontally disposed; and
   (d) a plurality of spaced apart discrete ridges which upwardly project from the top surface of the base, each of the plurality of discrete ridges intersecting the reference plane, the base, first prong, second prong, and plurality of ridges being formed as an integrally molded unit comprised of plastic.

19. A line keep as recited in claim 18, wherein at least one ridge is disposed between the first location and the second location.

20. A line keep as recited in claim 18, wherein the first prong can be repeatedly and manually moved between a vertically upstanding position and folded over positioned, the first finger being self-retained in the folded over position.

21. A line keep for retaining a line comprising:
   (a) a base having a top surface and an opposing bottom surface;
   (b) a first prong upwardly projecting from the top surface of the base at a first location and terminating at a freely exposed first finger; and
   (c) a second prong upwardly projecting from the top surface of the base at a second location spaced apart from the first prong, the second prong terminating at a freely exposed second finger, the second prong being configured such that when the line is disposed between the first and second prong, the second prong can be repeatedly and manually moved between an upstanding position and a folded positioned wherein the second prong is bent over so that the second finger is disposed adjacent to the line; and
   (d) a plurality of spaced apart discrete ridges which upwardly project from the top surface of the base, each of the plurality of discrete ridges intersecting the reference plane.

22. A line keep as recited in claim 21, wherein the second finger is self-retained in the folded position.

23. A line keep as recited in claim 21, wherein the base, the first prong, and the second prong are integrally molded as a unit comprised of plastic.

24. A line keep as recited in claim 23, wherein the plastic has a Flexural Strength at Yield in a range between about 8,000 psi and about 12,000 psi.

25. A line keep as recited in claim 23, wherein the plastic is comprised of PCTG.

26. A line keep as recited in claim 21, further comprising a plurality of line keeps, each line keep having a different color.

* * * * *

UNITED STATES PATENT AND TRADEMARK OFFICE
CERTIFICATE OF CORRECTION

PATENT NO. : 6,134,754
DATED : October 24, 2000
INVENTOR(S) : Christopher Hansson; Fred P. Lampropoulos; Arlin D. Nelson; William Padilla; Garlyn W. Hendry It is certified that error appears in the above-identified patent and that said Letters Patent is hereby corrected as shown below:

Column 1,
Line 51, before "guidewire" delete "the"

Column 2,
Line 58, after "securely" change "position" to -- positioned --

Column 3,
Line 40, after "shapes" change "SO" to -- so --

Column 6,
Line 20, after "securely" change "position" to -- positioned --

Column 8,
Line 44, after "first" change "pong" to -- prong --

Column 9,
Line 33, after "over" change "positioned" to -- position --

Column 10,
Line 14, after "folded" change "positioned" to -- position --

Signed and Sealed this

Thirteenth Day of November, 2001

*Attest:*

NICHOLAS P. GODICI
*Acting Director of the United States Patent and Trademark Office*

*Attesting Officer*